United States Patent [19]

Pfab et al.

[11] Patent Number: 5,502,213

[45] Date of Patent: Mar. 26, 1996

[54] PURIFICATION OF CRUDE PYRROLES

[75] Inventors: Peter Pfab, Limburgerhof; Peter Wahl, Ladenburg; Dieter Franz, Ludwigshafen, all of Germany

[73] Assignee: BASF Aktiengesellschaft, Ludwigshafen, Germany

[21] Appl. No.: 184,689

[22] Filed: Jan. 21, 1994

[30] Foreign Application Priority Data

Jan. 23, 1993 [DE] Germany ............ 43 01 776.2

[51] Int. Cl.⁶ .................... C07D 207/32
[52] U.S. Cl. ............ 548/564; 548/560; 548/579
[58] Field of Search .................... 548/560, 564, 548/579

[56] References Cited

U.S. PATENT DOCUMENTS

| | | | |
|---|---|---|---|
| 3,555,021 | 1/1971 | Beutel et al. | 260/250 |
| 4,384,125 | 5/1983 | Goettsch et al. | 548/555 |
| 5,039,817 | 8/1991 | Kroker et al. | 548/543 |
| 5,116,466 | 5/1992 | Marquis et al. | 203/58 |

FOREIGN PATENT DOCUMENTS

| | | | |
|---|---|---|---|
| 515865 | 6/1939 | United Kingdom | 548/560 |
| 852130 | 10/1960 | United Kingdom | 546/257 |

OTHER PUBLICATIONS

CA 106(7): 50031p Purification of N–methylpyrrolidone. Tomita et al., p. 626, 1987.

*Primary Examiner*—Joseph K. McKane
*Attorney, Agent, or Firm*—John H. Shurtleff

[57] ABSTRACT

A process for purifying crude pyrroles obtained in the preparation of pyrroles of the general formula I

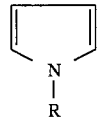

I where R is hydrogen or a $C_1$–$C_6$-alkyl radical, which comprises treating the mixture containing the crude pyrrole with an acid or an activated carboxylic acid derivative and removing the pyrrole from the mixture by distillation at reduced pressure and at a bottom temperature of up to 160° C.

11 Claims, No Drawings

PURIFICATION OF CRUDE PYRROLES

The present invention relates to a process for purifying crude pyrroles obtained in the preparation of pyrroles of the general formula I

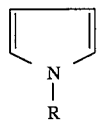

where R denotes hydrogen or a $C_1$–$C_6$-alkyl radical.

Pyrroles and pyrrole derivatives can be prepared by various processes (see eg. Ullmanns Encyklopädie der technischen Chemie (Ullmann's Encyclopedia of Industrial Chemistry), 4th edition Vol. 19, pp. 639–642). A possibility consists in dehydrating pyrrolidines in the presence of certain catalysts (see eg. GB 515 865 and EP 67 360 B1).

A difficulty in the preparation of pyrroles is in isolating the pyrrole in pure form after the reaction. According to EP 67 360 B1, to do this the mixture is worked up by distillation which, however, often does not lead to sufficiently pure products. It is known from GB 515 865 to wash N-phenylpyrrole with dilute HCl and then to sublime it. The sublimation of the solid N-phenylpyrrole, however, is laborious.

What is important here is in particular the most complete possible removal of the pyrrolidines, which is particularly difficult on account of the azeotropes formed between pyrrole, pyrrolidine and water.

It is an object of the present invention to make available a process for purifying crude pyrrole which leads to highly pure products and is simple to carry out in terms of process engineering.

We have found that this object is achieved by a process for purifying crude pyrroles obtained in the preparation of pyrroles of the general formula I

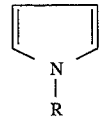

where R is hydrogen or a $C_1$–$C_6$-alkyl radical, which comprises treating the mixture containing the crude pyrrole with an acid or an activated carboxylic acid derivative and then removing the pyrrole from the mixture by distillation at reduced pressure and a bottom temperature of up to 160° C.

It emerges that, as a result of the combination of the reaction with an acid or an activated carboxylic acid derivative and subsequent distillative working up, pyrroles having a residual water content of less than 0.2% and a pyrrolidine content of less than 0.3% can be obtained.

If it is intended that the pyrrolidine content should be particularly low, it is preferred that the mixture containing the crude pyrrole is treated with an at least 10% strength by weight mineral or carboxylic acid and the pyrrole is removed from the mixture by distillation at 300 mbar—20 mbar and a bottom temperature from 60° C. to 90° C.

It is crucial here that the bottom temperature is adjusted to be in the range indicated, otherwise increased amounts of impurities occur.

The mineral acid employed is in particular sulfuric acid; the carboxylic acid formic acid, preferably 60 to 95% strength by weight formic acid. If it is intended to recover again the pyrrolidine removed by the reaction with acid, a process is expediently used in which the mixture containing the crude pyrrole is treated with a 10 to 30% strength by weight mineral or carboxylic acid and the aqueous phase formed is removed before the distillative working up of the pyrrole. The pyrrolidine can be recovered from the aqueous phase after suitable pH adjustment.

If it is intended that the water content in the pyrrole should be particularly low, it is preferred that the mixture containing the crude pyrroles is treated with heating with an activated carboxylic acid derivative with the formation of amides and the pyrrole is removed from the mixture by distillation at pressures from 1000 mbar to 200 mbar and bottom temperatures from 80° C. to 160° C. In this procedure, a water content in the pure pyrrole of less than 0.1% can be achieved.

Suitable activated carboxylic acid derivatives are eg. carboxylic anhydrides, carbonyl chlorides or carboxylic esters. Methyl or ethyl esters of $C_1$–$C_3$-monocarboxylic acids, in particular methyl formates, are preferred.

In the distillative work-up taking place after the reaction with acid or activated carboxylic acid derivatives, a small amount of forerun initially passes over, which can be fed back into the crude pyrrole.

It is expedient to subject the crude pyrrole to a predistillation before the reaction with the acid or the activated carboxylic acid derivative. This can be carried out eg. such that the pyrroles are removed from the bottom residue at a reduced pressure of up to 40 mbar and a bottom temperature of up to 85° C. The forerun in this predistillation contains about 80% of pyrrole, 15% of pyrrolidine and 3% of water and can be fed back into the crude pyrrole; the water-clear main fraction contains about 95% by weight of the pyrrole originally present.

The present purification process is particularly highly suitable for crude pyrroles which are prepared by reacting pyrrolidines of the formula II

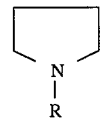

where R has the meaning indicated above, at from 160° C. to 400° C. in the presence of supported palladium catalysts which contain basic compounds of the alkali metals or alkaline earth metals and/or rare earth metals and/or elements of the groups Ib, IIb, VIIb, cobalt and/or nickel.

The pyrrole can be recovered particularly conveniently from the reaction mixtures obtained in this preparation procedure, which contain, inter alia, pyrroles and pyrrolidines, by means of the present working-up process.

The respective proportions of pyrroles and pyrrolidines were determined by gas chromatography using an FID as the detector. The pyrrole content of the crude solution was determined after calibration with an internal standard. The water content was determined according to Fischer.

EXAMPLES

In all examples described in the following, a batchwise, oil bath-heated, 1 liter vacuum rectification apparatus was used. The mirrored 30 mm vacuum jacket glass column was 300 mm long and was packed with stainless steel wire gauze helices (φ3 mm). The reflux could be passed through a water separator. All examples were carried out using a reflux ratio of 1:1.

EXAMPLE 1

Recovery of a Predistillate 500 g of crude pyrrole, which had been prepared by dehydrating pyrrolidine up to 275° C. on a supported palladium catalyst as disclosed in Example 8 of EP 67360 B1 (0.5% by weight palladium, 1.0% by weight manganese, 5.0% by weight cerium(IV) oxide on alumina grain size 0.2 to 0.6 mm), were rectified. According to GC analysis, the crude pyrrole contained 72% pyrrole, 14% pyrrolidine and 1% low-boiling components (alkyl-substituted pyrroles and pyrrolidines, data in % by weight). According to Karl Fischer, the water content was 4%. The first fraction was recovered at a constant 150 mbar, the second at 150–110 mbar and the third at 110–40 mbar. The bottom temperature rose from 80° C. at the start to 110° C. 8 g of a water phase separated from the first fraction. The organic phase (40 g, passing over up to 79° C.) contained 65% pyrrole, 10% pyrrolidine, 12% water and 13% low-boiling components. The second fraction (285 g, head temperature 79°–80° C.) contained 81% pyrrole, 16% pyrrolidine and 3% water. The third fraction (100 g, passing over 8020 –54° C.) contained 86% pyrrole and 14% pyrrolidine. Calculated over all fractions, 95% of the pyrrole employed could be recovered.

Fractions 2 and 3 were combined and employed in Examples 2–5 as "predistillates".

EXAMPLE 2

500 g of predistillate were treated with 113 g of 50% strength sulfuric acid and 84 g of water. 203 g of aqueous phase were removed. The organic phase was rectified, initially working under a vacuum of 200 mbar. After 63 g of forerun containing 78% pyrrole, the first main fraction (200 g, passing over at 84° C.) containing >97% pyrrole, 2% water and <0.1% pyrrolidine was recovered. In the course of the second main fraction (100 g) the column pressure was lowered to 40 mbar. The bottom temperature was kept below 100° C. The analyses showed >99% pyrrole, 0.6% water and <0.1% pyrrolidine. The distillation was discontinued at a bottom temperature of 110° C. The last fraction (33 g) contained 0.3% pyrrolidine and >99% pyrrole. If a balance is carried out over all fractions, 95% of the pyrrole employed was distilled over.

EXAMPLE 3

500 g of predistillate were adjusted to pH 7 using 59 g of formic acid. 52 g of water were separated at normal pressure. After a forerun of 60 g, a main fraction (200 g, head temperature 65° C.) having a pyrrole content of >99% was recovered at 85 mbar. The water content, like the pyrrolidine content of the main fractions, was <0.1% in each case.

EXAMPLE 4

500 g of predistillate were treated with 225 g of a 25% strength methanolic sulfuric acid. Methanol was removed by distillation at normal pressure and the pressure was reduced to 85 mbar. After 60 g of forerun, a main fraction of 200 g was taken (85° C. head temperature). The pyrrolidine content was <0.1%.

EXAMPLE 5

500 g of predistillate were treated with 70 g of methyl formate with water-cooling. The mixture was heated under reflux at normal pressure for 6 h. During the course of this, excess methyl formate passed into the exhaust gas. The mixture was rectified at 85 mbar. After 60 g of forerun, a main fraction of 200 g was recovered (85° C. head temperature) having a water content, like a pyrrolidine content of <0.1%.

EXAMPLE 6

Without Predistillation 16 g of water were separated from 500 g of crude pyrrole using 120 g of cyclohexane. The cyclohexane was stripped off at 350 mbar. 69 g of methyl formate were then added. The solution was distilled at a vacuum of 40 mbar and a maximum bottom temperature of 160° C. 97% of the pyrrole employed passed over in pyrrolidine-free form (<0.1%).

It thus surprisingly emerged that highly pure pyrrole could also be obtained without predistillation.

We claim:

1. A process for purifying crude pyrroles containing pyrrolidine impurities as obtained in the preparation of pyrroles of the general formula I

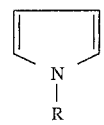

where R is hydrogen or a $C_1$–$C_6$-alkyl radical, which comprises treating the crude pyrrole with an acid or an activated carboxylic acid derivative and removing the pyrrole from the resulting mixture by distillation at reduced pressure and a bottom temperature of up to 160° C.

2. A process as claimed in claim 1, wherein the mixture containing the crude pyrrole is treated with an at least 20% strength by weight mineral or carboxylic acid and the pyrrole is removed from the mixture by distillation at 300 mbar–20 mbar and a bottom temperature from 60° C. to 90° C.

3. A process as claimed in claim 2, wherein the mineral acid employed is sulfuric acid.

4. A process as claimed in claim 2, wherein the mixture containing the crude pyrrole is treated with a 10 to 30% strength by weight mineral or carboxylic acid and the aqueous phase formed is removed before the distillative work-up of the pyrrole.

5. A process as claimed in claim 2, wherein the carboxylic acid employed is a 60 to 95% strength by weight formic acid.

6. A process as claimed in claim 1, wherein the mixture containing the crude pyrroles is treated with an activated carboxylic acid derivative with heating or cooling and the pyrrole is removed from the mixture by distillation at pressures from 1000 mbar to 200 mbar and bottom temperatures from 80° to 160° C.

7. A process as claimed in claim 6, wherein the activated carboxylic acid derivatives employed are methyl or ethyl esters of $C_1$–$C_3$-monocarboxylic acids.

8. A process as claimed in claim 1, wherein the crude pyrroles to be purified are obtained by dehydrating pyrrolidines of the formula II

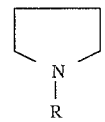

where R has the meaning indicated in claim 1, at from 160° C. to 400° C. in the presence of supported palladium catalysts which contain basic compounds of the alkali metals or alkaline earth metals and/or rare earth metals and/or elements of the groups Ib, IIb, VIIb, cobalt and/or nickel.

9. A process as claimed in claim 1, wherein the crude pyrrazole is subjected to a predistillation at gradually reduced pressures and gradually increased bottom temperatures in order to substantially reduce its water content prior to its treatment with an acid or activated carboxylic acid derivative.

10. A process as claimed in claim 9, wherein the predistillation is carried out at an initial reduced pressure of about 150 mbar and a bottom temperature of about 80° C. to recover a first fraction containing an increased proportion of water and pyrrolidine impurities and a decreased proportion of pyrrole, and the pressure is then gradually reduced over a range of from 150 to 40 mbar as the bottom temperature is gradually increased over a range of from 80° C. to 110° C. to recover subsequent fractions having an increased proportion of pyrrole and a decreased proportion of water and pyrrolidine impurities for said treatment, said subsequent fractions being combined for said treatment with an acid or activated carboxylic acid derivative.

11. A process as claimed in claim 10, wherein said a water phase is separated from the organic phase of said first fraction and the organic phase is fed back into the crude pyrrole for said treatment with an acid or activated carboxylic acid derivative.

* * * * *